United States Patent [19]

Van Scoik et al.

[11] Patent Number: 5,234,696
[45] Date of Patent: Aug. 10, 1993

[54] METHOD OF PRODUCING TABLETS, TABLETS PRODUCED THEREBY, AND METHOD OF TREATMENT USING SAME

[75] Inventors: Kurt G. Van Scoik, Grayslake; Ernest R. Keske, Waukegan, both of Ill.; Kent L. Cipollo, Westerville; Jeffery K. Weis, Columbus, both of Ohio

[73] Assignee: Abbott Laboratories, Abbott Park, Ill.

[21] Appl. No.: 815,096

[22] Filed: Dec. 27, 1991

[51] Int. Cl.⁵ .................................. A61K 9/14
[52] U.S. Cl. ................................ 424/489; 424/464; 424/465; 424/474; 424/480; 514/960; 514/891
[58] Field of Search ............... 424/489, 474, 479, 480, 424/489, 493, 494

[56] References Cited

U.S. PATENT DOCUMENTS

| | | | |
|---|---|---|---|
| 4,228,099 | 10/1980 | Walser | 260/501.11 |
| 4,296,127 | 10/1981 | Walser | 424/319 |
| 4,320,146 | 3/1982 | Walser | 424/319 |
| 4,352,814 | 10/1982 | Walser | 424/273 |
| 4,897,270 | 1/1990 | Deutsch et al. | 424/465 |
| 4,908,214 | 3/1990 | Bobee et al. | 424/477 |
| 4,957,938 | 9/1990 | Anderson et al. | 514/412 |
| 5,137,732 | 8/1992 | Buehler et al. | 424/489 |

FOREIGN PATENT DOCUMENTS 0184999 6/1986 European Pat. Off. .

OTHER PUBLICATIONS

Walser, M., *Ketoacids in the Treatment of Uremia*, Clinical Nephrology, vol. 3, pp. 180–186 (1975).
Bergstram, J., et al., *Metabolic Studies with Keto Acids in Uremia*, The American Journal of Clinical Nutrition, vol. 31, pp. 1761–1766 (Oct. 1978).
Heiland, A., *Evaluation of Essential Amino Acids and Keto Acids in Uremic Patients on Low-Protein Diet*, The American Journal of Clinical Nutrition, 1784–1792 vol. 31, pp. (Oct. 1978).
Frohling, P. T., et al., *Conservative Treatment with Ketoacid and Amino Acid Supplemented Low-Protein Diets in Chronic Renal Failure*, vol. 33, pp. 1667–1673 (Jul. 1980).
Chronicled Sales Aid for Ketosteril ® Tablets. Dated May 1984–Fresenious AG Bad Homburg, Germany 3 pages.
Search Report—from H. Z. Stone to J. Weis dated Nov. 26, 1990 24 pages.

*Primary Examiner*—Thurman K. Page
*Assistant Examiner*—James M. Spear
*Attorney, Agent, or Firm*—Donald O. Nickey; Lonnie R. Drayer

[57] ABSTRACT

Dietetic formulations for oral use are described, made up of tablets formed from dense granules of mixtures of keto- or hydroxy-amino acid analogs, possibly coated by protective films, which are dissolved in the gastrointestinal juices. The process for obtaining dense granules includes a coordinated increase in pressure being maintained for a substantial period of time and subsequent tableting and possible coating by immersion or spraying of the granular material.

17 Claims, No Drawings

METHOD OF PRODUCING TABLETS, TABLETS PRODUCED THEREBY, AND METHOD OF TREATMENT USING SAME

TECHNICAL FIELD

The present invention relates to a method of preparing a tablet of a powdered substance, a tablet made thereby, and a method of treatment using such a tablet. In one embodiment, the method of the present invention is used to prepare a tablet of a multicomponent powdered substance used in the nutritional treatment of chronic renal failure.

BACKGROUND

The use of tablets is a common method of administration of therapeutic substances in solid form. Such substances may include, for instance, medications and dietary supplements. There are several advantages to tableting. Tablets reduce bulk, making swallowing easier, and provide an alternative to liquid solutions or suspensions. Coated tablets help to preserve the table contents and also reduce or mask unpleasant taste and/or odor.

A number of problems can present themselves in therapeutic systems which use low density substances, substances which are chemically unstable and/or substances having unpleasant taste or odors. One example of such a system is that used in the treatment of chronic renal failure. These systems generally comprise a combination of amino acids and keto- and hydroxy-analogues thereof. Examples of these systems are described in U.S. Patents to Walser U.S. Pat. Nos. 4,228,099; 4,296,127; 4,320,146; and 4,352,814; U.S. Pat. No. 4,908,214 to Bobee, et al.; U.S. Pat. No. 4,957,938 to Anderson, et al.; and European Patent application No. 0 184 999 to Iaccherl, all of which are hereby incorporated herein by reference. A major problem associated with these systems is that the component materials have low bulk density and must be consumed at relatively high daily dosages. Another problem attendant to these systems is that many of the components present organoleptic concerns (i.e. those related to the taste, smell, appearance, mouthfeel, etc.). For example, ornithine $\alpha$-ketoisocaproate, lysine $\alpha$-keto-$\beta$-methylvalerate, histidine $\alpha$-ketoisocaproate, tryptophan, and calcium $\alpha$-hydroxy-$\gamma$-methylthiobutyrate are extremely bitter. Also, volatile decomposition products of the components, such as isovaleric acid, methylbutyric acid, and isobutyric acid, have very unpleasant odors. Other components, such as tyrosine, have a gritty mouth feel. These problems of sensory acceptance make oral administration of such untableted systems very unpalatable for the patients.

Presently these problems are addressed by the oral administration of solvated or suspended powders in highly flavored liquids. This technique deals with the low bulk density by presenting the therapeutic substance in liquid form while the flavoring masks the unpleasant taste and odor. However, some of the problems associated with this method are the unacceptability of the liquid to a segment of the population, and the complexity and expense of manufacturing, packaging and transporting a liquid formulation. Also, the formulation often must be wholly or partially reconstituted which can complicate administration, particularly in systems requiring high daily dosages. In addition, the presence of the flavoring agents has the potential for degradation of the active components when in aqueous solution or suspension.

Another alternative presently used is the production of tablets using a wet granulation process. This known process eliminates the problems of low bulk density and air entrapment. This process involves the use of a solution or binder added to the dry powder accompanied by some type of physical mixing action. In this method, the binder solution is intended to wet the surface of the powder particles or crystals, thereby displacing air which is present in the pores and interstices. This method often provides some dissolution of the powdered substance by the binder solution, which assists in densifying the material when the compaction and subsequent drying processes are complete. Wet granulation can be carried out using either aqueous or alcohol-based binder solutions. Although the wet granulation method has been successful in many applications, some potential problems remain. The binder solution will solvate some of the powder components which can accelerate degradation reactions. Once the wet-granulated powder is compressed into tablet form, small amounts of remaining solvent will accelerate degradation of the components.

Another approach to the densification of powdered substances has been that of "slugging" the material. "Slugging" comprises compressing large tablets of the material on a tableting machine. This process requires that the powdered substance have suitable flow characteristics and be amenable to compression so as to form a compacted material which survives ejection from the tablet die. Many powder materials, such as those used in the treatment of chronic renal failure discussed above, do not compress well enough to form a sufficiently strong compact to survive ejection from the tablet die, even at extremely low speeds. Other components, while moderately compressible and capable of forming a compact, require slow ejection from the die in order to maintain a compacted state. Accordingly, slugging is not feasible for renal systems.

There are other problems that specifically relate to the tableting formulations used in the treatment of chronic renal failure. Since these materials are nutritional agents (or their biochemical precursors) rather than typical pharmaceutical agents, a large amount of the powder blend must be consumed. For example, a typical patient may have to consume a daily dosage of 25 grams to receive the therapeutic benefits and avoid negative nitrogen balance. It is well known in the area of pharmaceuticals that many patients, particularly pediatric and geriatric patients, have a difficult time swallowing either large tablets or large numbers of tablets. Some of this difficulty may be mechanical (e.g. esophageal stricture, insufficient saliva, esophageal spasm due to gag reflexes), but it may also have a significant psychological component. The patients may come to dread swallowing large tablets which cause discomfort or a choking sensation.

It is well known that tableting excipients can be effective in improving compressibility and compactability of powders. In some systems, it may be possible to add large quantities of these excipients (e.g. microcrystalline cellulose, lactose, compressible sugar, dicalcium phosphate, and the like) to the powder blend, and directly improve the tableting characteristics of the material. However, this would necessitate making the tablets much larger or requiring the patients to consume many more tablets. Both of these alternatives are undesirable or unacceptable from the point of view of compliance.

In view of the foregoing problems existing in the prior art, and the desired objectives and advantages to be achieved in a tableted substance, the medical community has long sought a tablet which is chemically stable, is of a size which can be easily swallowed, and does not have an offensive taste or odor.

SUMMARY OF THE INVENTION

Toward the solution of the above-discussed problems and in order to achieve the desired advantages pointed out above, there is disclosed a method of preparing a tablet of a powdered substance, a tablet made thereby, and a method of treatment using such a tablet. Thus, this invention discloses a method of preparing a tablet from a powdered mixture, said method comprising the following steps:

(a) obtaining a powdered mixture comprising at least one material selected from the group consisting of amino acids, keto acids and conjugates and salts thereof;

(b) subjecting said powdered mixture to a compaction carried out over sufficient time and at sufficient pressure so as to remove air from said powder and cause physical granulation in said powder and yielding a compacted material containing granules;

(c) liberating said granules from said compacted material;

(d) compressing said granules resulting from step (c) into a tablet; and (e) providing said tablet with a coating.

There is further disclosed the above method wherein said compaction comprises raising the pressure on said powdered mixture from below about 400 pounds per square inch (p.s.i.) to a pressure in the range of about 600 p.s.i., within a period of time in range of from about 1 second to about 5 seconds.

The powdered substances to which the inventive method may be applied include any substance reduced to or produced in powder form; that is, in a state of fine, loose particles; such as by crushing, grinding, disintegration, precipitation from a liquid, drying, etc. Such substances may be of natural or of synthetic origin, and may be crystalline. The powdered substance may be a single substance or a mixture of two or more substances. Accordingly, as used herein, the term "powdered substance" shall mean any substance produced in powder form or reduced to powder form.

The method of the present invention may be most advantageously applied to powdered substances which have a low bulk density or which may be chemically unstable during or as a result of their formation into tablets by wet granulation or as a liquid solution or suspension. The substances which may be used in the present invention may include any therapeutic substance or placebo. Representative of the powdered substances that may be used in accordance with the method of the present invention include amino acids, particularly essential or semi-essential amino acids and/or the keto-acid or hydroxy-acid analogues thereof and mitures thereof. Such substances may be in the form of salts, for example calcium or magnesium salts.

Accordingly, as a specific embodiment of the present invention there is disclosed a method of preparing a tablet of a powdered substance which comprises a mixture of the following components present in the following percentages by weight ranges:

| | |
|---|---|
| L-ORNITHINE α-KETOISOVALERATE | 20–25 |
| L-ORNITHINE α-KETOISOCAPROATE | 20–25 |
| L-LYSINE α-KETO-β-METHYLVALERATE | 20–25 |
| L-HISTIDINE α-KETOISOCAPROATE | 5–9 |
| CALCIUM, SODIUM OR POTASSIUM SALT OF-α-HYDROXY-γ-METHYLTHIOBUTYRATE | 1–3 |
| L-TRYPTOPHAN | 0.1–1 |
| L-TYROSINE | 15–20 |
| L-THREONINE | 3–7; |

Another specific embodiment of the present invention utilizes a mixture of the following components present in the following percentages by weight:

| | |
|---|---|
| L-ornithine α-ketoisovalerate | 20–25% |
| L-ornithine α-keto-β-methylvalerate | 20–25% |
| L-lysine α-ketoisocaproate | 20–25% |
| L-histidine α-ketoisocaproate | 5–9% |
| calcium, sodium or potassium salt of α-hydroxy-γ-methylthiobutyrate | 1–3% |
| L-tryptophan | 0.1–1% |
| L-tyrosine | 15–20% |
| L-threonine | 3–7% |

STEPS OF THE PRESENT INVENTIVE METHOD

The First Step—Compaction to Form Granules by Physical Granulation and Separation of Granules from Compacted Material The method of the present invention involves two fundamental steps. In the first step, the powdered substance is subjected to a specified compaction which is carried out over a sufficient time and a sufficient pressure so as to remove air from the powdered substance and cause physical granulation in the powdered substance. The removal of air should be understood as including the removal of any interstitial gas from the powdered substance. Physical granulation as used herein is intended to mean the conversion of a powdered substance into granules or grains by the application of pressure and substantially without the action of a solvent or other carrier liquid. Physical granulation may include any form of physical aggolmeration whereby the powdered substance is held in an integral physical form. As used herein, physical granulation is intended to mean granulation brought about substantially solely by the application of pressure without the use of a solvent or other liquid. This is in contrast to so-called "wet" granulation which utilizes a liquid solvent or other liquid to assist in the removal of entrained air from the powdered substance prior to the formation of a tablet.

Although not limited to any particular theory of action, but rather to provide a more complete disclosure of the invention, it is thought that a relatively slow and even rate of compression and compaction in the first processing step (i.e. compaction) allows sufficient time for efficient removal or reduction of entrapped air and allows a sufficient number of particle to particle bonds to be created for granule formation. These granules are then able to survive decompression. A material of a highly elastic nature will tend to recover in an elastic fashion after compaction, resulting in cohesive failure and a return to the initial powder state. If the compaction is slow enough to allow plastic deformation to occur along with the elastic deformation, then it is possible for the material to relax slowly and, upon removal of compressive forces the material will remain an intact compact. Furthermore, the compaction can be conducted with cooling processes to avoid thermal stress.

This first step also involves the liberation of the granulated material from the compacted material, such as from a wafer produced by some compaction machinery. The compaction step of the present invention is carried out at a rate which is much slower than conventional tableting methods. Typical compaction operations of the prior art are too fast to allow physical granulation to occur. Such prior art compaction steps occur at high speed with compaction times estimated to be on the order of a fraction of a second.

Although the invention in its most general form is not limited to any specific compaction pressure range, it has been found that roll compaction of amino acid/keto acid/analog mixtures (renal formulations) of the type described herein is carried out most advantageously from about 400 p.s.i. to about 600 p.s.i. Normally, below 400 p.s.i. roll compaction is difficult to achieve, while the product obtained using roll compaction above 600 p.s.i. has been found to have inferior stability characteristics.

It is preferred that the rolls compactor be chilled to reduce thermal stress on the compacted material. Generally, the lower the temperature, the greater the reduction in thermal stress. The practice of the present invention is not limited to the use of a chilled roll compactor or to any range of temperatures to which such rolls might be cooled. However, a representative temperature range for chilled compactor rolls is from about 5° to about 20° C., typically about 10° C.

Where the powdered substance comprises one or more amino acids, keto acids, or their analogues, it is preferred that the compaction step comprise raising the pressure on the powder from a pressure below 400 p.s.i. (normally atmospheric pressure; about 14.7 p.s.i) to a pressure within a range of from about 400 p.s.i. to about 600 p.s.i. The rise in pressure should occur over a period of time in the range from about 1 second to about 5 seconds. This granulation step may be carried out on any appropriate equipment commonly used or known in the art. For example, the compaction or granulation may be carried out by means of a roll compaction unit, such as a Chilsonator ®, commercially available from Fitzpatrick Company. Where such equipment is used, an elongated compacted wafer is produced. A wafer may be described as a flat sheet of material with uniformly disposed, rounded protruding ribs oriented perpendicular to the flow of the material through the compaction unit (formed by the relief of the compaction roller).

The wafers are then milled, such as by the use of a hammermill, commercially available from Fitzpatrick Company or Fluid Air Company to obtain appropriately sized granules. It is preferred that the granules be separated from any fines, such as by sifting. The preferred fines content of the granules should be below about 5% by weight.

The granules to be tableted may also include excipient materials. The excipient material(s) are preferably admixed with the granules subsequent to the separation of the granules from the compacted material. Representative of the excipient materials useful in this invention include microcrystalline cellulose (such as Avicel PH101), magnesium stearate, talc, calcium phosphate, maltodextrin and soy fiber. It is preferred that microcrystalline cellulose be dried to a moisture content in the range from about 0.75% to about 1.25% by weight (and preferably 1% by weight) as measured by loss upon drying. Such drying is preferred because excess water will react with formulation components while an overly dry mixture tends to interfere with the tableting process. Sodium starch glycolate (such as ExploTab ®, commercially available from Edward Mendell Company), may also be used as an optional ingredient for its function as a disintegrant.

The Second Step—Formation of a Tablet

After the granules are produced, the second step in the method of the present invention involves compressing the granules into a tablet. This may be done with conventional tableting equipment. An example of such tableting equipment is a high speed rotary tableting machine, commercially available from Fette Company, or its equivalent.

The tablets produced may be of any size and shape appropriate for oral administration to humans or other animals as the particular application requires. A typical tablet shape and size used in oral administration of renal formulations in humans is an ovoid tablet about 0.82 inches in length and 0.39 inches in width.

After the tablets are formed they are preferably coated to improve their stability and their organoleptic properties. Optionally, a subcoating, such as titanium dioxide or other inert, preferably opaque substances, may be used to improve the cosmetic appearance of the tablet and/or to improve stability by serving to better insulate the active ingredients from the environment and/or the flavored outer coating.

The tablet is normally provided with at least an outer coating. This coating may include any tablet coating known in the art as appropriate to achieve the desired coloring and flavoring characteristics, in view of the active tablet components. The coating may provide for the appropriate dosage delivery rate and/or situs (such as whether the active ingredients are to be time-released or whether released in the stomach or in the bowel). The coating may be applied, for instance, using a Accella-Cota ® machine, commercially available from Thomas Company. In the case of tablets made from renal formulations it has been found that a coating, such as hydroxypropyl methylcellulose, provides a satisfactory gloss coating. Because the renal formulations are sensitive to heat and moisture, it is also desirable to use a coating which can be dissolved in a coating solvent that is predominately alcohol (i.e. ethanol). The choice of this alcohol coating also allows the coating process to be carried out at relatively low temperatures, minimizing thermal stress and exposure to moisture during the coating process. Other materials used in the coating process may include, hydroxypropyl cellulose and polyethylene glycol. With respect to coatings, it is preferred that non-aldehyde coatings be used with the renal formulations.

The coating may also be provided with one or more flavoring agents. These may be selected from any commercially available natural or synthetic flavoring agents, flavors, etc. An examples of such a flavoring agent is a coconut flavoring from Firmenich Company of Switzerland. The coconut macaroon flavoring number 367-57-04/T, commercially available from Firmenich is preferred for the renal formulations. As can be seen in the experimental results discussed below, the vanilla flavoring is not preferred for use with renal formulations however, vanilla may be appropriate for use with other formulations.

DETAILED DESCRIPTION OF THE PREFERRED EMBODIMENT

The following is a description of a preferred embodiment of the present invention, which is also presently considered to be the best mode of carrying out the invention for the specific active tablet components described below in Table 1 (hereinafter referenced to as the RKAP formulation) wherein the acrinym RKAP is understood hereinafter to refer to the abbreviation for renal keto analog product). Unless indicated otherwise all percentages herein are expressed as percent by weight. The value of the present invention is demonstrated in several time stability studies.

EXAMPLE I

A tablet was produced from a powdered renal formulation. The powdered formula comprises a mixture of components set out in Table I.

TABLE I

| RKAP Formula | | |
|---|---|---|
| COMPONENT | WT % | Grams/ 2Kg |
| L-ORNITHINE α-KETOISOVALERATE | 22.5 | 440.8 |
| L-ORNITHINE α-KETOISOCAPROATE | 22.2 | 444.4 |
| L-LYSINE α-KETO-β-METHYL-VALERATE | 23.4 | 468.0 |
| L-HISTIDINE α-KETOISOCAPROATE | 6.9 | 138.0 |
| CALCIUM α-HYDROXY-γ-METHYL-THIOBUTYRATE | 2.1 | 41.0 |
| L-TRYPTOPHAN | 0.3 | 6.0 |
| L-TYROSINE | 17.5 | 350.8 |
| L-THREONINE | 5.1 | 101.0 |
| TOTAL | 100.0 | 2000.0 |

The bulk RKAP powder was prepared by mixing the various components at the recited weight percentages. The powder was stored under refrigeration. The powdered material was subjected to physical granulation by means of a Chilsonator ® roll compaction unit. The pressure for the roll compactor was set for 400–600 p.s.i. and had a residence time of about 2 seconds. The wafer that was produced was subsequently milled by use of a hammermill, to obtain the appropriately sized granules. The preferred granule size is in the range from about 149 to about 2,000 microns. After milling, the granules were sifted to remove fines (preferably less than 5% fines by weight) and then dry-blended with excipients as set out in Example II.

EXAMPLE II

TABLE II

| RKAP Tablet Composition Including Excipients | | | |
|---|---|---|---|
| Formula for 1000 tablets: | | | |
| Mg/Tablet | Item | | Amount (g) |
| 930.0 | 1. RKAP Granules (Example I) | | 930.00 |
| 95.3 | 2. Microcrystalline cellulose | | 95.30 |
| 16.9 | 3. Magnesium stearate | | 16.90 |
| 16.9 | 4. Talc, USP | | 16.90 |

The granules of the RKAP formulation, microcrystalline cellulose, magnesium stearate and talc were blended for ten minutes in a V-blender. The mixture was tableted using a Fette machine. The tablets were formed by compression of the Table II composition through sufficient force to yield a tablet with a thickness of approximately 7.3 to 7.4 mm and a hardness of 9 to 11 Strong-Cobb units (S.C.U.). A machine speed of 25 to 50 rpm was used with a full set of punches. At 25 rpm, approximately 925 tablets per minute were produced.

EXAMPLE III

The tablets are then coated. In this case, two coatings are used. The first coating is a subcoating whose formulation is shown in Table III.

TABLE III

| Subcoating Formula For RKAP Tablet | | |
|---|---|---|
| Item | % W/Vol | Amount |
| 1. Hydroxypropyl Methyl-cellulose 2910, 6CPS | 2.5 | 500.0 gm |
| 2. Hydroxypropyl Cellulose, NF | 0.4 | 80.0 gm |
| 3. Titanium Dioxide | 2.0 | 400.0 gm |
| 4. Polyethylene Glycol USP | 1.0 | 200.0 gm |
| 5. Water, purified USP distilled | 10.0 | 2.0 L |
| 6. Ethanol, SD3A, 200 proof | q.s. | 18.0 L |

The formulation in Table III was applied at the rate of 0.5 liters for each kilogram of tablets from Example III. To prepare this subcoating, two liters of the ethanol were placed into a mixing tank and the hydroxypropyl methylcellulose and polyethylene glycol were added with stirring. The water was then added and mixing was continued until a clear solution was obtained. The titanium dioxide was placed in a mill with enough ethanol to cover the material, and the mixture was milled for 30 minutes. The milled material was then discharged into the clear solution and the mixing was continued for at least one hour.

The subcoating was applied using atomizing guns. After the subcoating was applied, a gloss coating was placed on the tablets. The gloss coating formulation is set out in Table IV.

TABLE IV

| Flavored Gloss Coating Formula For RKAP Tablet | | |
|---|---|---|
| Item | % W/V | Amount |
| 1. Hydroxypropyl Methyl-cellulose 2910, 6CPS | 4.0 | 800.0 gm |
| 2. Flavor, Firmenich 367-57-04/T 30 gms in Propylene Glycol | 1.0 | 200.0 gm |
| 3. Water, purified USP distilled | 10.0 | 1.9 L |
| 4. Ethanol, SD3A, 200 proof | q.s. | 18.0 L |

The gloss coating was prepared by placing ten liters of ethanol into a suitable container. The hydroxypropyl methylcellulose and flavor in propylene glycol were added with stirring. This was followed by the addition of the water and the solution was mixed for about one hour. Finally, ethanol was added to the solution until a volume of 20.0 liters was obtained. 0.3 liters of the solution was applied per 1.0 kilograms of the RKAP tablets from Examples II or III. The gloss coating formula was applied using methods known in the art, specifically by atomizing guns.

EXAMPLE V

In another embodiment, the RKAP formulation of Table I was mixed with the disintegrant-sodium starch glycolate (ExploTab ®, commercially available from Edward Mendell Company) after separation of the granules by milling. This formulation is shown in Table IA below:

TABLE IA

RKAP Tablet Formulation With 2% Sodium Starch Glycolate (Disintegrant)

| Component | % By Weight | Amount |
|---|---|---|
| RKAP Grams | 87.8 | 18.0 kg |
| Microcrystalline Cellulose Avicel PH101 (dried) | 7.0 | 1435. gm |
| ExploTab ® (sodium starch glycolate) | 2.0 | 400. gm |
| Magnesium Stearate | 1.6 | 328. gm |
| Talc | 1.6 | 328. gm |

To prepare the formulation in Table IA, the microcrystalline cellulose was placed on paper lined trays in an oven at about 60° C. (±5° C.) and dried to not more than 1.25% but not less than 0.75% (as close to 1.0% as possible) water. The dried microcrystalline cellulose, the sodium starch glycolate, and the RKAP granules (as prepared in Example I) were placed in an appropriate sized V-blender and blended for five minutes. The magnesium stearate and talc were then added to the V-blender and blended for an additional 5 minutes. A Fette machine was used to produce the tablets as in Example II.

EXAMPLE VI

The RKAP tablets were prepared as in Example V with the exception that 1% sodium starch glycolate was used. The formulation for the 1% sodium starch glycolate is shown in Table IB.

TABLE IB

RKAP Tablet With 1% Sodium Starch Glycolate (ExploTab ®)

| Component | % By Weight | Amount |
|---|---|---|
| RKAP Granules | 87.8 | 6.0 kg |
| Microcrystalline Cellulose Avicel PH101 (dried) | 8.0 | 547. gm |
| ExploTab ® (sodium starch glycolate) | 1.0 | 69. gm |
| Magnesium Stearate | 1.6 | 109. gm |
| Talc | 1.6 | 109. gm |

EXAMPLE VII

The tablets prepared in Examples V and VI were subcoated with the formulation set out in Table III. The subcoating formula presented in Table III provided an opaque coating over the tablet core. The final outer/gloss coating for the tablets is set out in Table IIA.

TABLE IIA

Gloss Coating for RKAP Tablets Containing Sodium Starch Glycolate (ExploTab ®)

| Component | % Weight by Volume | Amount |
|---|---|---|
| Hydroypropyl Methylcellulose | 4.0% | 1.1 kg |
| Firmenich Flavor #367-57-04/T | 4.0% | 300.0 gm |
| Water, Purified, (USP Distilled) | 10.0% | 3.0 L |
| Alcohol (SD3A 200 proof) | qs | 27.0 L |

The outer/gloss coating was prepared by placing the hydroypropyl methylcellulose and the water in 20 liters of alcohol with continued mixing. When a visually clear solution was obtained, the FIRMENICH Flavor #367-57-04/T in propylene glycol was added and mixing was continued for about 10 minutes. The final volume was adjusted to 30 liters by the addition of alcohol. Mixing was continued for approximately 15 minutes. To coat the tablet with both the opaque and gloss coating liquids, a spraying system such as 7310.1/4 JAU automatic air atomizing guns with a 2850 fluid cap and a 134255-45 aircap was used. The pan speed was set at between 7 and 9 rpm. The spray guns were positioned between 7" and 9" from the tablet bed, with the spray directed above the halfway point on the tablet bed. The inlet air controlling temperature was set at 50° C., and the exhaust air was set at 35° to 40° C.

EXAMPLE VIII

A tablet was prepared in accordance with Example II with the exception that the RKAP formulation was as follows:

| Component | % by weight |
|---|---|
| L-ORNITHINE α-KETOISOVALERATE | 20.0 |
| L-ORNITHINE α-KETOISOCAPROATE | 25.0 |
| L-LYSINE α-KETO-β-METHYLVALERATE | 25.0 |
| L-HISTIDINE α-KETOISOCAPROATE | 7.5 |
| CALCIUM α-HYDROXY-γ-METHYLTHIOBUTYRATE | 3.0 |
| l-TRYPTOPHAN | 0.5 |
| L-TYROSINE | 16.0 |
| L-THREONINE (Thr) | 3.0 |

EXAMPLE IX

A tablet was prepared in accordance with the method of Example II with the exception that the RKAP formulation is as follows:

| Component | % by weight |
|---|---|
| L-ORNITHINE α-KETOISOVALERATE | 24.0 |
| L-ORNITHINE α-KETOISOCAPROATE | 22.0 |
| L-LYSINE α-KETO-β-METHYLVALERATE | 21.0 |
| L-HISTIDINE α-KETOISOCAPROATE | 7.0 |
| CALCIUM α-HYDROXY-γ-METHYLTHIOBUTYRATE | 2.3 |
| l-TRYPTOPHAN | 0.7 |
| L-TYROSINE | 18.0 |
| L-THREONINE | 5.0 |

EXAMPLE X CONTROL

This experiment was conducted to evaluate of effect of granulation at pressures greater than 600 psi. The RKAP formula of Table I was granulated as set out in Example I except that the roll pressure of the Chilsonator ® roll compaction unit was set at above 600 psi. After milling, shifting, and tableting as set out in Example II the tablets were evaluated. A low hardness value of 13.2 S.C.U. was obtained and a visible pink color in the tablet was apparent. These problems and others made the tablets unsatisfactory for clinical use. It is speculated that tablet softness was due to granulation at pressures in excess of 600 psi, as was the undesirable pink color. When RKAP powder is compressed, it is believed that the component crystals plastically deform and fracture, resulting in satisfactory bonding primarily through Van der Waals forces. When the tablets were formed the plastic deformation of microcrystalline cellulose is relied upon in conjunction with some residual Van der Waals bonding. When RKAP is granulated at pressures above 600 psi the residual Van der Waals forces are used up. Thus, above 600 psi the microcrystalline cellulose alone must form and hold the tablet intact, thus resulting in softer tablets which were easier to crush.

humidities. Results are reported as a percentage of theoretical target on an as is basis.

TABLE VI

Loss of Purity Study

| DAYS | THR (%) | TYR (%) | HIS (%) | ORN (%) | LYS (%) | KIV (%) | HMTB (%) | TRP (%) | KMV (%) | KIC (%) |
|---|---|---|---|---|---|---|---|---|---|---|
| | | | | | 30° C. | | | | | |
| 0 | 97.0 | 97.1 | 97.9 | 101.1 | 103.9 | 98.8 | 101.6 | 96.6 | 97.4 | 98.3 |
| 30 | 96.8 | 96.8 | 95.7 | 99.9 | 102.1 | 97.4 | 100.8 | 95.4 | 96.0 | 91.0 |
| 64 | 99.4 | 95.6 | 92.1 | 99.5 | 100.1 | 98.9 | 98.3 | 100.0 | 96.2 | 83.2 |
| 93 | 100.2 | 97.7 | 91.3 | 99.8 | 99.9 | 98.6 | 99.2 | 98.9 | 97.3 | 79.4 |
| 94 | 101.0 | 97.7 | 91.8 | 101.1 | 101.6 | 96.8 | 99.0 | 98.7 | 96.0 | 76.9 |
| 182 | 104.0 | 100.4 | 93.6 | 100.8 | 100.1 | 93.0 | 91.2 | 97.1 | 93.6 | 67.4 |
| 183 | 100.7 | 98.2 | 89.4 | 98.9 | 98.1 | 91.6 | 90.2 | 96.2 | 92.6 | 65.4 |
| 454 | 100.3 | 99.6 | 84.0 | 90.8 | 93.6 | 69.8 | 67.7 | 84.4 | 88.7 | 41.6 |
| | | | | | 40° C. | | | | | |
| 0 | 97.0 | 97.1 | 97.9 | 101.1 | 103.9 | 98.8 | 101.6 | 96.6 | 97.4 | 98.3 |
| 30 | 98.3 | 99.1 | 88.6 | 99.4 | 99.0 | 89.4 | 93.8 | 85.7 | 93.4 | 62.0 |
| | | | 50% Relative Humidity/Open Bottle/23° C. | | | | | | | |
| 0 | 97.0 | 97.1 | 97.9 | 101.1 | 103.9 | 98.8 | 101.6 | 96.6 | 97.4 | 98.3 |
| 30 | 96.5 | 96.5 | 96.6 | 100.7 | 103.2 | 96.8 | 99.2 | 86.7 | 94.7 | 95.6 |
| 64 | 97.3 | 95.2 | 93.9 | 98.8 | 101.6 | 98.8 | 98.6 | 98.9 | 96.0 | 90.7 |
| 93 | 97.9 | 96.1 | 93.5 | 99.4 | 102.1 | 97.1 | 99.4 | 67.3 | 97.3 | 92.7 |
| 94 | 97.8 | 96.1 | 93.0 | 99.5 | 102.6 | 96.6 | 99.2 | 68.6 | 96.7 | 92.7 |
| | | | 50% Relative Humidity/Closed Bottle/23° C. | | | | | | | |
| 0 | 97.0 | 97.1 | 97.9 | 101.1 | 103.9 | 98.8 | 101.6 | 96.6 | 97.4 | 98.3 |
| 30 | 96.9 | 97.0 | 97.8 | 100.9 | 103.3 | 99.2 | 101.4 | 95.7 | 96.5 | 96.6 |
| 64 | 99.4 | 96.1 | 96.8 | 99.9 | 102.4 | 100.1 | 100.3 | 100.0 | 97.1 | 92.7 |
| 93 | 101.0 | 97.8 | 98.1 | 101.3 | 103.5 | 100.9 | 102.7 | 100.5 | 98.4 | 93.3 |
| 94 | 100.7 | 96.4 | 97.6 | 101.2 | 103.3 | 101.2 | 102.9 | 101.1 | 99.2 | 94.1 |
| 182 | 104.5 | 99.3 | 100.9 | 101.7 | 103.1 | 100.0 | 100.1 | 103.7 | 97.2 | 89.3 |
| 183 | 101.1 | 98.1 | 97.4 | 101.3 | 103.1 | 99.1 | 97.9 | 102.9 | 96.2 | 88.7 |

EXAMPLE XI CONTROL

This experiment was conducted to evaluate the use of a wet-granulation process on RKAP powder. RKAP powder (Table I) was blended in a Patterson-Kelley dry-blender equipped with an intensifier bar and subjected to ethanol granulation and compression. The ingredients are listed in Table V. The RKAP, the Avicel PH 101 and Povidone (K-30) were dissolved in 180 ml of alcohol. This mixture was hand screened with a 4 mesh screen and dried at room temperature. The powder was then hand screened using a 10 mesh screen and then the lubricants were blended therewith for five minutes. This mixture was compressed into a tablet as described in Example II.

TABLE V

WET GRANULATION STUDY TABLET COMPOSITION

| | Mg/Tablet | Amount |
|---|---|---|
| 1. RKAP Powder | 1000 | 295 gm |
| 2. Avicel PH 101 | 153 | 45 gm |
| 3. Talc | 17 | 5 gm |
| 4. Magnesium stearate | 17 | 5 gm |
| 5. Povidone (K-30) | 7.5 | 2.21 gm |
| 6. Ethanol, 200 pf | — | as needed |

It was not possible, even using ethanol to granulate, to achieve a granule dense enough to achieve the desired tablet weight. Roll compaction at between about 400 and 600 psi allows enough densification to get proper fill weight (active material per tablet) and also avoid solvents.

EXPERIMENTAL RESULTS

Loss of purity studies were conducted on the tablets from Example II that were subcoated and gloss coated according to Examples III and IV. Stability of RKAP components was studied at various temperature and Threonine (Thr), tyrosine (Tyr), histidine (His), ornithine (Orn), and lysine (Lys) contents were determined by amino acid analysis. Total ketoisovaleric acid (KIV), total hydroxymethylthiobutyrate (HMTB), tryptophan (Trp), total ketoisocaproic acid (KIC), and ketomethylvaleric acid (KMV) levels were quantitated by HPLC. All samples were analyzed on a weight/weight "as is basis". No corrections were made in the reported data for moisture uptake, moisture loss, residual solvent loss, and/or volatilization of degradation products that might have occurred during storage.

The foregoing results show that in tablet form all of the active components of RKAP are stable at room temperature for at least 28 days under normal packaging conditions.

LOSS OF PURITY STUDY—364 DAYS OF STORAGE

RKAP tablets prepared according to examples were enrolled in an accelerated storage stability program along with a powder control to assess the keeping quality characteristics of tablets vs. powder. Analysis of RKAP components was conducted by HPLC and amino acid analysis. The product is considered to be stable if the loss of purity does not exceed the estimated experimental error of ±3%.

RKAP (Table I) bulk powder was used. Uncoated RKAP tablets (Example II) and coated RKAP tablets from Example VII were also used. The RKAP control powder was filtered through a 12 mesh screen and placed in sample bottles. The tablets were prepared using the ingredients and tablet manufactures procedures of Example II. One-half of the resulting uncoated tablets were then coated with coating formula according to Example III. The uncoated tablets, coated tablets, and a powder control were enrolled in the accelerated RKAP stability program to assess the impact of "phys cal" granulation on tablet stability. The tablets were stored for 364 days at 5° C. in sealed scintillation vials. The tablets were also stored for 364 days at 25° C., 70 days at 37° and 43° C. in foil covered scintillation vials. The powder control was stored for 364 days at 5° C. in sealed 4 ounce jars, and 43° C. in foil covered jars. The humidities were ambient for the variables stored at 25° C., 37° C., and 43° C.

RKAP tablet stability data through 70 days at 43° and 37° C., and 364 days at 25° and 5° C. is summarized in Table VII. RKAP powder control data through 70 days at 43° C., and 364 days at 5° C. is also summarized in Table VIII. Results are reported as a percentage of theoretical target.

TABLE VII

| | | \multicolumn{10}{c}{RKAP TABLET STABILITY} |
| | | COMPONENT | | | | | | | | |
| TABLET | DAYS | THR (%) | TYR (%) | HIS (%) | ORN (%) | LYS (%) | KIV (%) | HMTB (%) | TRP (%) | KMV (%) | KIC (%) |
|---|---|---|---|---|---|---|---|---|---|---|---|
| | | | | | 43° C. | | | | | | |
| Coated | 0 | 99.0 | 94.5 | 96.1 | 96.7 | 99.3 | 96.5 | 95.3 | 115.1 | 93.2 | 99.4 |
| | 4 | 99.1 | 95.0 | 92.9 | 97.2 | 98.6 | 95.6 | 94.9 | 109.8 | 92.6 | 91.1 |
| | 7 | 99.8 | 95.5 | 92.6 | 97.9 | 98.4 | 93.5 | 93.5 | 107.7 | 91.4 | 84.1 |
| | 10 | 101.3 | 97.5 | 89.3 | 98.3 | 98.6 | 93.7 | 90.5 | 113.7 | 90.6 | 77.9 |
| | 14 | 100.2 | 97.2 | 88.6 | 97.4 | 97.6 | 96.2 | 94.0 | 116.7 | 94.3 | 76.9 |
| | 29 | 100.9 | 98.4 | 87.1 | 96.1 | 97.1 | 92.1 | 89.9 | 115.8 | 91.9 | 64.7 |
| | 42 | 100.4 | 97.9 | 84.6 | 93.9 | 94.5 | 93.7 | 89.8 | 117.8 | 88.7 | 58.1 |
| | 70 | 104.3 | 101.1 | 85.1 | 94.3 | 93.7 | 90.8 | 86.9 | 114.1 | 85.6 | 46.5 |
| Powder | 0 | 101.0 | 98.5 | 98.2 | 99.6 | 101.9 | 96.0 | 95.2 | 113.0 | 93.1 | 99.8 |
| | 4 | 103.1 | 100.6 | 99.5 | 101.1 | 102.2 | 86.2 | 88.2 | 100.5 | 84.5 | 84.1 |
| | 7 | 102.8 | 100.1 | 99.6 | 101.7 | 102.1 | 90.3 | 92.0 | 104.6 | 88.8 | 83.0 |
| | 10 | 103.8 | 101.8 | 97.6 | 101.3 | 101.3 | 96.9 | 94.5 | 114.2 | 93.1 | 80.9 |
| | 14 | 101.9 | 100.5 | 100.0 | 99.8 | 99.2 | 94.5 | 91.2 | 112.6 | 90.7 | 74.2 |
| | 29 | 101.5 | 100.0 | 97.2 | 98.0 | 89.3 | 92.3 | 92.0 | 117.2 | 93.5 | 67.9 |
| | 42 | 102.9 | 102.7 | 98.7 | 98.9 | 98.2 | 94.0 | 89.4 | 120.7 | 92.3 | 63.4 |
| | 70 | 105.3 | 104.8 | 100.0 | 99.5 | 97.1 | 94.3 | 87.3 | 121.5 | 89.3 | 58.4 |
| Uncoated | 0 | 100.7 | 97.0 | 98.3 | 99.2 | 101.9 | 96.5 | 95.9 | 113.8 | 93.9 | 99.8 |
| | 4 | 101.3 | 97.4 | 95.9 | 99.5 | 101.2 | 97.7 | 97.4 | 112.8 | 94.4 | 94.5 |
| | 7 | 102.2 | 97.4 | 94.4 | 100.3 | 101.2 | 98.8 | 97.6 | 112.6 | 94.9 | 88.4 |
| | 10 | 103.5 | 100.1 | 92.3 | 100.5 | 101.2 | 97.8 | 94.9 | 118.3 | 93.8 | 82.6 |
| | 14 | 102.1 | 99.1 | 91.5 | 98.7 | 99.8 | 94.5 | 92.4 | 113.1 | 91.0 | 74.7 |
| | 29 | 101.4 | 98.6 | 86.8 | 96.3 | 97.6 | 93.1 | 89.8 | 115.2 | 91.2 | 64.9 |
| | 42 | 103.2 | 100.2 | 87.0 | 96.0 | 97.1 | 94.5 | 89.8 | 118.5 | 90.3 | 59.7 |
| | 70 | 105.5 | 102.2 | 86.9 | 95.6 | 95.9 | 91.4 | 89.1 | 118.7 | 82.6 | 47.7 |
| | | | | | 37° C. | | | | | | |
| Un-Coated | 0 | 100.7 | 97.0 | 98.3 | 99.2 | 101.9 | 96.5 | 95.9 | 113.8 | 93.9 | 99.8 |
| | 7 | 103.2 | 99.1 | 98.3 | 100.6 | 103.1 | 90.0 | 89.5 | 103.0 | 87.3 | 88.9 |
| | 14 | 101.6 | 98.4 | 95.8 | 101.5 | 102.3 | 98.4 | 95.6 | 120.6 | 95.8 | 91.2 |
| | 29 | 101.4 | 97.1 | 91.6 | 97.0 | 98.7 | 96.5 | 92.4 | 110.9 | 94.0 | 80.4 |
| | 42 | 102.5 | 99.4 | 94.0 | 100.2 | 101.8 | 96.3 | 93.9 | 115.7 | 94.4 | 76.6 |
| | 70 | 104.4 | 100.6 | 93.2 | 100.1 | 100.8 | 95.0 | 92.4 | 115.9 | 92.9 | 67.9 |
| Coated | 0 | 99.0 | 94.5 | 96.1 | 96.7 | 99.3 | 96.5 | 95.3 | 115.1 | 93.2 | 99.4 |
| | 7 | 100.1 | 95.9 | 94.7 | 97.6 | 99.6 | 92.8 | 93.7 | 106.1 | 90.3 | 91.6 |
| | 14 | 99.5 | 96.7 | 94.0 | 100.6 | 100.8 | 95.8 | 95.6 | 110.0 | 93.0 | 88.3 |
| | 29 | 98.9 | 95.0 | 88.3 | 95.1 | 96.6 | 95.7 | 88.9 | 110.4 | 93.3 | 80.7 |
| | 42 | 101.0 | 97.8 | 93.4 | 98.8 | 99.5 | 94.6 | 91.1 | 113.7 | 93.1 | 75.9 |
| | 70 | 101.5 | 97.0 | 88.9 | 96.9 | 96.8 | 93.6 | 89.9 | 114.0 | 93.2 | 67.7 |
| | | | | | 25° C. | | | | | | |
| Un-Coated | 0 | 100.7 | 97.0 | 98.3 | 99.2 | 101.9 | 96.5 | 95.9 | 113.8 | 93.9 | 99.8 |
| | 14 | 100.9 | 97.5 | 98.5 | 99.8 | 102.0 | 96.8 | 95.0 | 118.6 | 93.4 | 97.2 |
| | 29 | 99.7 | 96.4 | 97.7 | 98.7 | 100.9 | 96.8 | 92.0 | 110.6 | 94.1 | 97.2 |
| | 70 | 102.2 | 97.9 | 97.4 | 100.7 | 102.5 | 98.0 | 97.4 | 109.5 | 96.0 | 97.8 |
| | 126 | 104.0 | 98.1 | 97.9 | 100.5 | 101.5 | 97.6 | 97.8 | 108.7 | 95.6 | 94.9 |
| | 238 | 101.5 | 99.3 | 97.7 | 101.2 | 102.2 | 95.7 | 96.4 | 108.3 | 95.6 | 89.0 |
| | 294 | 106.0 | 102.6 | 99.9 | 104.9 | 106.6 | 95.2 | 91.7 | 106.8 | 94.3 | 84.5 |
| | 364 | 98.0 | 97.9 | 92.6 | 98.6 | 100.2 | 96.2 | 95.0 | 104.5 | 95.7 | 82.6 |
| Coated | 0 | 99.0 | 94.5 | 96.1 | 96.7 | 99.3 | 96.5 | 95.3 | 115.1 | 93.2 | 99.4 |
| | 14 | 97.9 | 94.7 | 95.1 | 97.1 | 99.1 | 93.8 | 94.9 | 107.2 | 90.5 | 93.6 |
| | 29 | 96.7 | 92.8 | 92.7 | 94.3 | 97.1 | 95.7 | 91.7 | 109.6 | 93.0 | 96.4 |
| | 70 | 100.0 | 95.4 | 95.3 | 98.5 | 100.2 | 96.3 | 95.5 | 107.3 | 94.8 | 96.3 |
| | 126 | 101.5 | 96.4 | 96.4 | 99.1 | 100.1 | 96.4 | 96.1 | 107.0 | 94.3 | 93.9 |
| | 238 | 98.7 | 95.9 | 93.3 | 97.7 | 98.2 | 94.6 | 94.5 | 106.8 | 94.2 | 88.4 |
| | 294 | 102.3 | 99.5 | 96.1 | 101.5 | 102.5 | 93.8 | 89.8 | 106.0 | 93.4 | 84.9 |
| | 364 | 96.5 | 96.7 | 91.1 | 97.6 | 99.3 | 94.1 | 91.9 | 101.9 | 93.7 | 82.0 |
| | | | | | 5° C. | | | | | | |
| Powder | 0 | 101.0 | 98.5 | 98.2 | 99.6 | 101.9 | 96.0 | 95.2 | 113.0 | 93.1 | 99.8 |
| | 29 | 98.9 | 99.0 | 98.4 | 99.3 | 100.9 | 98.1 | 97.3 | 112.6 | 94.3 | 99.9 |
| | 70 | 99.7 | 97.7 | 97.9 | 99.0 | 100.5 | 97.8 | 97.4 | 112.3 | 94.9 | 99.8 |
| | 98 | 100.7 | 98.3 | 95.9 | 99.4 | 101.1 | 98.7 | 98.0 | 113.9 | 96.1 | 98.3 |
| | 126 | 99.8 | 98.5 | 98.4 | 99.5 | 100.7 | 97.7 | 97.9 | 110.7 | 94.2 | 98.3 |
| | 238 | 99.5 | 98.3 | 99.6 | 99.4 | 100.7 | 96.7 | 97.2 | 111.2 | 94.6 | 98.7 |
| | 364 | 97.7 | 98.7 | 97.5 | 99.6 | 101.9 | 98.5 | 97.8 | 103.8 | 95.6 | 97.9 |
| Un-Coated | 0 | 100.7 | 97.0 | 98.3 | 99.2 | 101.9 | 96.5 | 95.9 | 113.8 | 93.9 | 99.8 |
| | 29 | 99.1 | 95.9 | 97.5 | 97.8 | 100.6 | 98.8 | 93.1 | 115.2 | 95.3 | 99.1 |
| | 70 | 100.8 | 96.7 | 99.1 | 99.9 | 101.7 | 96.7 | 97.0 | 110.6 | 94.5 | 98.0 |

TABLE VII-continued

RKAP TABLET STABILITY

| TABLET | DAYS | THR (%) | TYR (%) | HIS (%) | ORN (%) | LYS (%) | KIV (%) | HMTB (%) | TRP (%) | KMV (%) | KIC (%) |
|---|---|---|---|---|---|---|---|---|---|---|---|
| | 98 | 101.3 | 96.6 | 94.8 | 99.8 | 102.1 | 99.3 | 96.8 | 115.1 | 96.8 | 99.8 |
| | 126 | 103.0 | 96.8 | 98.9 | 99.8 | 101.4 | 98.5 | 98.4 | 113.7 | 95.9 | 99.5 |
| | 238 | 99.2 | 97.0 | 99.5 | 99.3 | 101.0 | 94.6 | 95.5 | 107.8 | 93.9 | 97.0 |
| | 364 | 96.5 | 96.3 | 95.9 | 98.1 | 100.5 | 97.0 | 95.7 | 110.8 | 95.2 | 97.7 |
| Coated | 0 | 99.0 | 94.5 | 96.1 | 96.7 | 99.3 | 96.5 | 95.3 | 115.1 | 93.2 | 99.4 |
| | 29 | 97.1 | 94.1 | 95.1 | 95.9 | 98.7 | 97.0 | 94.5 | 112.7 | 94.2 | 98.1 |
| | 70 | 98.1 | 93.9 | 96.2 | 97.1 | 98.8 | 95.7 | 96.0 | 109.6 | 93.7 | 97.4 |
| | 98 | 101.0 | 96.5 | 94.8 | 99.6 | 101.4 | 98.4 | 96.1 | 114.3 | 95.6 | 98.9 |
| | 126 | 100.9 | 94.6 | 96.7 | 97.6 | 99.3 | 96.0 | 96.0 | 110.5 | 93.7 | 97.0 |
| | 238 | 98.9 | 95.4 | 97.0 | 98.1 | 100.4 | 95.0 | 96.1 | 110.6 | 94.0 | 97.4 |
| | 364 | 94.4 | 94.0 | 93.5 | 95.6 | 97.7 | 98.1 | 97.1 | 111.8 | 95.6 | 97.8 |

DISCUSSION

The coated and uncoated RKAP tablets were stable for less than 4 days at 43° C. due to ketoisocaproic acid (KIC) decomposition (8.3% and 5.3% loss, respectively). Coated and uncoated RKAP tablet stability decreased after 14 days of storage due to decomposition of ketoisocaproic (KIC) (22.5 and 25.1%), and histidine (His) (7.5 and 6.8%), respectively. Storage of the coated and uncoated tablets for 70 days at 43° C. resulted in ketoisocaproic acid (KIC) losses of 52.9% and 52.1%, respectively, while the powder control showed a ketoisocaproic acid (KIC) loss of 41.4%. Under these conditions (70 days at 43° C.), the tablets exhibited component losses in histidine (His) (11.0 and 11.4%), ornithine (Orn) (2.4 and 3.6%), lysine (Lys) (5.6 and 6.0%), ketomethylvaleric acid (KMV) (7.6 and 11.6%), ketoisovaleric acid (KIV) (5.1 and 5.7%), and hydroxymethylthiobutyrate (HMTB) (6.8 and 8.4%), while the powder control displayed component losses in lysine (Lys) (4.8%), ketomethylvaleric acid (KMV) (3.8%), and hydroxymethylthiobutyrate (HMTB) (7.9%). Although uncoated and coated RKAP tablets manufactured by the physical granulation method were of similar stability, several components such as histidine (His), ketomethylvaleric acid (KMV), and ketoisovaleric acid (KIV) showed significantly greater losses in tablets (uncoated and coated) than in the powder control. The reasons for these observations are unclear, but due to the tableting process, and the more intimate component interaction present in the tablet form, these losses are not surprising.

The coated and uncoated RKAP tablets were stable for less than 7 days at 37° C. due to a 7.8% and 8.6% ketoisocaproic acid (KIC) loss, respectively. Storage of the tablets for 70 days at 43° C. resulted in component losses of histidine (His) (5.1 and 7.2%), hydroxymethylthiobutyrate (HMTB) (3.5 and 5.4%) and ketoisocaproic acid (KIC) (31.7 and 31.9%).

The coated and uncoated RKAP tablets were stable for at least 70 days at 25° C., but less than 126 days, due to a 5.5% and 4.9% ketoisocaproic acid (KIC) loss, respectively. Similar KIC losses for both tablet variables were observed after 364 days in storage, 17.4% for coated tablets and 17.2% for uncoated tablets. Apparent tryptophan (Trp) losses of 13.2% from coated tablets and 9.3% from uncoated tablets after 364 days of storage was most likely due to tablet homogeneity and/or experimental error rather than tryptophan (Trp) decomposition, since tryptophan is present at 0.3% in the formulation. Importantly, there was no tryptophan loss in either the coated or uncoated tablets after storage for 70 days at 37 or 43° C.

All of the RKAP components in the uncoated RKAP tablets, the coated RKAP tablets, and the RKAP powder control were stable for at least 364 days at 5° C.

CONCLUSIONS

All of the RKAP components in the uncoated tablets, the coated tablets, and the powder control were stable for at least 364 days of storage at 5° C., for at least 70 days at 25° C., for less than 7 days at 37° C., and for less than 4 days at 43° C. Although tablets (uncoated and coated) made by the physical granulation method, and powder exhibited similar stabilities, several components-histidine (His), ketomethylvaleric acid (KMV), and ketoisocaproic acid (KIC) exhibited somewhat increased tablet decomposition compared to powder after extended periods of storage at higher temperature (43° C.).

The most heat sensitive RKAP tablet component, ketoisocaproic acid (KIC), showed losses of 4.9 and 5.5% after 126 days of storage at 25° C., and losses of 7.8 and 8.6% after 7 days of storage at 37° C., and losses of 5.3 and 8.3% after 4 days of storage at 43° C. Longer storage (70 days) of the RKAP tablets and RKAP powder control at 43° C. suggested that ketoisocaproic acid (KIC) will be the stability limiting component under recommended storage conditions of 5° C. Furthermore, similar RKAP component losses were observed for the coated and uncoated tablets under the experimental conditions of this study.

As ketoisocaproic acid (KIC) is the shelf life limiting component of RKAP tablets, the method of the present invention produced tablets that are chemically stable for as long as 24 months when stored at refrigerated temperatures. While the degradation or the disappearance of any particular RKAP component reflects the shelf stability of this product, it should be borne in mind the shelf life or "fitness of use" of tablets produced according to the present invention will depend on delivering a minimum specified amount of one or more components or on the types and levels of degradation products that form during the decomposition process.

EXAMPLE XII

Aromatic Evaluation and Loss of Purity Study of Five Flavored RKAP Tablet Coatings The RKAP bulk powder formulation (Table I) was used in the preparation of both flavored (5 different variables) and unflavored tablets (control). These six experimental tablets, designated A, B, C, D, E, and F respectively, were enrolled in an accelerated stability program and a sensory screening. RKAP tablet cores produced according to Example II were coated with five different flavored coatings as described in Example VII and evaluated by eight professional panelists for acceptable aromatics. The five flavored coatings studied were FIRMENICH flavors 367-57-01/T, -02/T, -03/T, -04/T and -05/T. The experimentals and the control are designated as follows:

A = RKAP control tablet with gloss coating/no flavor
B = RKAP tablet with flavored FIRMENICH coating 367-57-01/T
C = RKAP tablet with flavored FIRMENICH coating 367-57-02/T
D = RKAP tablet with flavored FIRMENICH coating 367-57-03/T
E = RKAP tablet with flavored FIRMENICH coating 367-57-04/T
F = RKAP tablet with flavored FIRMENICH coating 367-57-05/T.

Two of the five were found to be more acceptable than the other three. An aroma evaluation was conducted on the two more acceptable tablets by a large professional panel consisting of 66 people. There were two significant results:

1) Sample E (FIRMENICH 367-57-04/T) was significantly preferred over sample B (FIRMENICH 367-57-01/T) for aroma.

Analysis was based on a nine point scale with nine being "like extremely," one being "dislike extremely" and five being "neither like nor dislike", gave the following results:
Sample E = 5.00
Sample B = 4.58.

2) Sample B was rated significantly stronger than sample E.

Analysis based on a five point scale with five being "aroma much to strong", three being "just right", and one being "aroma definitely not strong enough", gave the following results:
Sample E = 3.41
Sample B = 3.79.

Tablet stability data through 42 days of storage at 43° C. and 37° C. is summarized in Tables VIII and IX, respectively.

TABLE VIII

RKAP STABILITY STUDY WITH FLAVORED COATINGS
Conditions: Temperature 43° C.

| TABLET | DAYS | THR (%) | TYR (%) | HIS (%) | ORN (%) | LYS (%) | KIV (%) | HMTB (%) | TRP (%) | KMV (%) | KIC (%) |
|---|---|---|---|---|---|---|---|---|---|---|---|
| A | 0 | 94.5 | 94.9 | 95.7 | 94.9 | 99.1 | 96.2 | 93.9 | 94.3 | 96.7 | 96.5 |
|   | 7 | 96.9 | 97.3 | 102.1 | 94.9 | 98.3 | 91.8 | 92.0 | 95.6 | 93.2 | 83.8 |
|   | 28 | 98.3 | 97.8 | 90.4 | 92.8 | 95.8 | 89.9 | 93.3 | 98.8 | 90.5 | 65.8 |
|   | 42 | 98.0 | 100.4 | 89.2 | 92.3 | 93.4 | 87.2 | 93.6 | 96.7 | 88.2 | 59.5 |
| B | 0 | 94.8 | 94.3 | 96.2 | 95.3 | 99.8 | 92.4 | 93.3 | 93.6 | 96.6 | 96.3 |
|   | 7 | 96.0 | 96.5 | 100.1 | 93.9 | 97.7 | 91.4 | 93.0 | 94.6 | 93.3 | 83.2 |
|   | 42 | 97.4 | 99.1 | 88.3 | 91.4 | 93.3 | 86.6 | 93.0 | 97.3 | 86.8 | 58.6 |
| C | 0 | 94.8 | 94.9 | 95.6 | 94.9 | 99.0 | 95.6 | 95.4 | 94.4 | 96.9 | 97.0 |
|   | 7 | 96.0 | 96.5 | 99.8 | 93.3 | 97.3 | 90.5 | 91.7 | 93.9 | 102.9 | 82.4 |
| D | 0 | 93.9 | 95.4 | 99.3 | 97.8 | 101.3 | 94.6 | 93.7 | 96.3 | 96.8 | 96.7 |
|   | 7 | 96.4 | 97.1 | 100.9 | 94.0 | 97.5 | 90.8 | 92.3 | 93.7 | 98.3 | 82.5 |
| E | 0 | 93.0 | 94.5 | 98.0 | 96.2 | 99.5 | 94.7 | 94.6 | 96.5 | 97.1 | 97.1 |
|   | 7 | 96.6 | 97.0 | 101.5 | 94.0 | 97.2 | 91.1 | 91.7 | 95.4 | 93.7 | 83.0 |
|   | 28 | 96.4 | 96.8 | 89.5 | 91.7 | 94.5 | 89.0 | 92.5 | 96.9 | 89.8 | 66.7 |
|   | 42 | 98.3 | 100.3 | 90.3 | 93.8 | 95.6 | 87.0 | 93.3 | 97.8 | 86.7 | 59.8 |
| F | 0 | 94.5 | 94.6 | 95.4 | 93.9 | 98.2 | 94.7 | 93.9 | 96.4 | 96.8 | 96.8 |
|   | 7 | 96.5 | 93.9 | 100.3 | 94.1 | 97.4 | 91.3 | 92.0 | 95.9 | 94.2 | 83.0 |

At 43° C. there were no significant differences in stability between any of the six tablet prototypes (Table VIII). All of the tablet prototypes were stable for less than 7 days of storage due to losses in ketoisocaproic acid.

TABLE IX

RKAP STABILITY STUDY WITH FLAVORED COATINGS
Conditions: Temperature 37° C.

| TABLET | DAYS | THR (%) | TYR (%) | HIS (%) | ORN (%) | LYS (%) | KIV (%) | HMTB (%) | TRP (%) | KMV (%) | KIC (%) |
|---|---|---|---|---|---|---|---|---|---|---|---|
| A | 0 | 94.5 | 94.9 | 95.7 | 94.9 | 99.1 | 96.2 | 93.9 | 94.3 | 96.7 | 96.5 |
|   | 28 | 96.3 | 96.7 | 96.0 | 94.8 | 98.2 | 91.1 | 91.7 | 95.4 | 92.2 | 76.0 |
|   | 42 | 98.8 | 98.1 | 93.5 | 94.6 | 98.1 | 91.7 | 94.9 | 95.9 | 94.0 | 71.9 |
| B | 0 | 94.8 | 94.3 | 96.2 | 95.3 | 99.8 | 92.4 | 93.3 | 93.6 | 96.6 | 96.3 |
|   | 28 | 96.1 | 96.7 | 94.2 | 93.6 | 96.8 | 92.2 | 93.3 | 96.5 | 93.2 | 76.5 |
|   | 42 | 98.1 | 98.7 | 92.7 | 93.9 | 98.4 | 90.7 | 93.9 | 95.4 | 92.6 | 71.3 |
| C | 0 | 94.8 | 94.9 | 95.6 | 94.9 | 99.0 | 95.6 | 95.4 | 94.4 | 96.9 | 97.0 |
|   | 28 | 96.2 | 97.1 | 93.9 | 94.2 | 97.8 | 92.1 | 93.0 | 96.1 | 93.9 | 75.2 |
| D | 0 | 93.9 | 95.4 | 99.3 | 97.8 | 101.3 | 94.6 | 93.7 | 96.3 | 96.8 | 96.7 |
|   | 28 | 96.5 | 97.4 | 94.7 | 94.6 | 97.9 | 92.3 | 93.0 | 96.5 | 94.0 | 75.4 |
| E | 0 | 93.0 | 94.5 | 98.0 | 96.2 | 99.5 | 94.7 | 94.6 | 96.5 | 97.1 | 97.1 |
|   | 28 | 96.3 | 96.4 | 92.5 | 93.4 | 96.8 | 91.7 | 93.0 | 96.5 | 93.5 | 75.4 |
|   | 42 | 96.6 | 98.6 | 91.6 | 95.4 | 97.7 | 91.0 | 94.2 | 95.9 | 93.2 | 71.1 |
| F | 0 | 94.5 | 94.6 | 95.4 | 93.9 | 98.2 | 94.7 | 93.9 | 96.4 | 96.8 | 96.8 |
|   | 28 | 96.2 | 96.7 | 92.1 | 93.6 | 97.1 | 92.4 | 91.1 | 96.5 | 94.2 | 75.7 |

At 37° C. there were no significant differences in stability between any of the six experimental tablets (Table IX). Storage of the control (A) and one of the flavored (E) tablet prototypes for 28 days resulted in component losses in ketoisocaproic acid (KIC) (20.5% and 21.7%), ketomethylvaleric acid (KMV) (4.5% and 3.6%), ketoisovaleric acid (KIV) (5.1% and 3.0%), histidine (His) (0% and 5.5%), and lysine (Lys) (3.3% and 5.0%), respectively.

All six experimental tablets (A–F) exhibited similar component stability to coated control tablets from the previous study. This example demonstrates that the method of this invention can produce a commercially viable flavored renal tablet.

EXAMPLE XIII

Control Wet Granulation Study

RKAP tablets produced by a wet granulation process (Example XI), were enrolled in an accelerated storage stability program to assess the keeping quality characteristics and evaluate a critical feature of this invention regarding slow and dry granulation of powdered renal formulae. RKAP component "loss of purity" was analyzed.

As previously described, RKAP component levels were quantitated by HPLC. All samples were analyzed on a weight/weight "as is basis". Compared to tablets prepared using the dry granulation process the experimentals showed significantly less component stability. This evidences the requirement that powdered renal formulae undergo a dry granulation process to produce a viable renal tablet.

EXAMPLES VIV

Loss of Purity Study-Excipients

RKAP powder (Table I) was used in the preparation of experimental tablets to evaluate the impact of excipients. 10 gms of RKAP powder was placed into a small glass jar and either 150 mg of magnesium stearate (sample I) or 150 mg of sodium stearyl fumarate (sample J) was added. The jars were mixed by hand for approximately 5 minutes by rotation and inversion, and were kept refrigerated. The resulting formulations were enrolled in an accelerated study to assess the impact of the excipients on stability. The samples (as powders) were stored in scintillation vials covered with aluminum foil for 25 days at 43° C. Component levels were quantitated by HPLC.

TABLE X

RKAP TABLET STABILITY STUDY - EXCIPIENTS TEMP 43°

| Tablet | Days | COMPONENT | | | | |
|---|---|---|---|---|---|---|
| | | KIC (%) | KIV (%) | KMV (%) | HMTB (%) | TRP (%) |
| Sample I | 0 | 98.4 | 97.5 | 94.8 | 97.8 | 125.2 |
| | 11 | 96.1 | 98.3 | 90.8 | 98.0 | 112.6 |
| | 15 | 95.2 | 98.1 | 89.1 | 97.4 | 112.4 |
| | 25 | 94.6 | 98.2 | 87.0 | 99.0 | 114.7 |
| Sample J | 0 | 97.9 | 97.2 | 94.1 | 97.3 | 125.8 |
| | 11 | 95.2 | 97.1 | 89.6 | 97.4 | 111.2 |
| | 15 | 93.6 | 96.3 | 87.4 | 96.0 | 110.4 |
| | 25 | 95.6 | 98.8 | 86.9 | 100.6 | 115.1 |

Stability data through 25 days at 43° C. is summarized in Table X above. Storage of Samples I and J resulted in losses of tryptophan (Trp) (10.5% and 10.7% degradation) and ketomethylvaleric acid (KMV) (7.8% and 7.2% degradation). The component ketoisocaproic acid (KIC) was not significantly more heat sensitive in the RKAP I powder (3.8%), than in the Sample J powder (2.3%). Consequently, there is no real preference as to which excipient is better from a heat stability standpoint. Magnesium stearate is a preferred RKAP excipient compared to sodium stearyl fumarate from a cost standpoint.

The RKAP powders used in this study were considerably more stable than the RKAP tablet prototypes used in the wet granulation study (Example XII), when stored under similar conditions. These observations indicate that RKAP components probably undergo additional stress in the "wet" granulation solvent process, which negatively impacts RKAP tablet shelf stability.

EXAMPLES XV

Control Loss of Purity Study-Wet Granulation (2nd Study)

Experimental RKAP tablets (designated Sample N, O, and P) were enrolled in an accelerated storage stability program to assess keeping quality characteristics of these wet-granulated formulations.

RKAP (Table I) powder was used in the preparation of sample tablets. RKAP formulation without histidine ketoisocaproate and RKAP formulation without ornithine ketoisocaproate were used in the preparation of samples O and N tablets. These formulations were blended in a dry blender from the individual components, equipped with an intensifier bar. The experimental powder formulations were individually subjected to ethanol granulation. Subsequent to wet granulation, histidine ketoisocaproate was added to the blend without same, while ornithine ketoisocaproate was added to the blend without same, since these components, respectively had been absent from the formulations in the granulation step. Sample P was RKAP powder of Table I. The formulations were then compressed into tablets according to Example II. The resulting uncoated tablets were enrolled in a accelerated study to assess the impact of the "wet" granulation step on tablet stability. The ingredients for samples N, O, and P are listed in Tables XI, XII and XII, respectively.

TABLE XI

Sample N Tablet Composition And Manufacturing Directions

| Item | Mg/Tablet | Amount |
|---|---|---|
| 1. RKAP without ornithine ketoisocaproate | 778 | 389.0 gm |
| 2. Ornithine ketoisocaproate | 222 | 111.0 gm |
| 3. Magnesium stearate | 17 | 8.5 gm |
| 4. Povidone (K-30) | 30 | 18.0 gm |
| 5. Ethanol, 200 pf USP | qs | as needed about 190 ml |

Sample N was prepared by dissolving the povidone in 100 ml of the ethanol which was used for wet granulation. The remaining ethanol was used and the sample was then dried in an air chamber overnight. The resultant was handscreened using 12 mesh screen. Ornithine ketoisocaproate was blended in for 5 minutes with the screened powder and then magnesium stearate was added and blended for 5 more minutes. The formulation was then tableted according to Example II.

TABLE XII

| | Sample O Composition | |
|---|---|---|
| Item | Mg/Tablet | Amount |
| 1. RKAP without histidine ketoisocaproate | 931 | 465.5 gm |
| 2. Histidine ketoisocaproate | 69 | 34.5 gm |
| 3. Magnesium stearate | 17 | 8.5 gm |
| 4. Povidone (K-30) | 30 | 18.0 gm |
| 5. Ethanol, 200 pf USP | qs | as needed about 190 ml |

Sample O was prepared in a manner similar to Sample N.

TABLE XIII

| | Sample P Composition | |
|---|---|---|
| Item | Mg/Tablet | Amount |
| 1. RKAP Ketoacid salts | 1000 | 500.0 gm |
| 2. Magnesium stearate | 17 | 8.5 gm |
| 3. Povidone (K-30) | 30 | 18.0 gm |
| 4. Ethanol, 200 pf USP | qs | as needed about 190 ml |

Sample P was prepared in a manner similar to Sample N.

Tablet stability data through 28 days at 43° C. is summarized in Table XIV. All three samples tested here were unstable in the ketoisocaproic acid (KIC) component after 7 days of storage at 43° C. The uncoated tablets were made with ornithine ketoisocaproate added after the "wet" granulation step (Sample N) and uncoated tablets made with histidine ketoisocaproate added after the wet granulation step (Sample O) were considerably more stable than uncoated tablets made with "wet" granulated RKAP powder (Sample P) after 28 days of storage at 43° C. In fact, under the above storage conditions Samples N and O underwent losses of 11.6% and 15.1% in KIC, 3.6% and 5.5% in KIV, and 5.4% in HMTB, In contrast Sample P underwent losses of 27.7% in KIC, 7.8% in KIV, and 9.6% in HMTB. Storage of the tablets for 7 days at 43° C. resulted in an tryptophan loss of 16.3%, 1.5%, and 11.6% for Sample N, O, and P respectively.

TABLE XIV

WET GRANULATION OF RKAP TABLETS STORED AT 43° C.

| Sample | Days | HMTB (%) | KIC (%) | KIV (%) | KMV (%) | TRP (%) |
|---|---|---|---|---|---|---|
| N | 0 | 95.6 | 99.6 | 99.6 | 89.5 | 111.7 |
|   | 7 | 95.0 | 93.4 | 100.7 | 87.6 | 95.4 |
|   | 14 | 96.3 | 92.1 | 98.8 | 86.8 | 93.0 |
|   | 21 | 91.3 | 85.0 | 94.8 | 81.7 | 90.3 |
|   | 28 | 90.2 | 88.0 | 86.0 | 81.4 | 94.4 |
| O | 0 | 94.1 | 97.0 | 104.6 | 86.2 | 96.6 |
|   | 7 | 93.6 | 92.8 | 99.7 | 85.1 | 95.1 |
|   | 14 | 91.2 | 88.5 | 101.1 | 82.7 | 97.9 |
|   | 21 | 88.2 | 84.4 | 97.4 | 76.4 | 97.0 |
|   | 28 | 88.7 | 81.9 | 99.1 | 77.3 | 98.4 |
| P | 0 | 98.2 | 98.0 | 98.7 | 93.5 | 110.5 |
|   | 7 | 96.5 | 85.0 | 95.8 | 92.7 | 98.9 |
|   | 14 | 92.3 | 80.1 | 94.4 | 94.3 | 97.8 |
|   | 21 | 94.2 | 76.8 | 93.8 | 92.7 | 97.6 |
|   | 28 | 88.6 | 70.3 | 90.9 | 88.0 | 93.4 |

The RKAP experimental tablets enrolled in this tablet study were unstable in ketoisocaproic acid after 5 days of storage at 43° C. This study did provide important information concerning the effects of the "wet" granulation step on RKAP stability. In this study, the uncoated tablets made with ornithine ketoisocaproate (Orn KIC) added after the "wet" granulation step (Sample N), and the uncoated tablets made with histidine ketoisocaproate (His KIC) added after the wet granulation step (Sample O) were considerably more stable than the uncoated tablets made with "wet" granulated RKAP powder (Sample P) after 28 days of storage at 43° C. This tablet stability data indicates that RKAP components undergo additional stress in the "wet" granulation solvent process, which negatively impacts the RKAP tablet shelf stability.

EXAMPLE XVI

Vanilla In The Coating

Experimental tablets were prepared according to Example I-IV except that vanilla flavoring was placed in the coating. When the vanillin flavored coating came into contact with the RKAP core there was a reaction which changed the color of the tablet from white to yellow. The sample had about double the degradation of ketoisocaproic acid (KIC) which is the result of the addition of the vanillin to the coating. Thus, the use of vanilla flavoring in the tablet coating is not a preferred embodiment of this invention.

EXAMPLE XVII

Wet Granulation

Tables XV and XVI present additional data comparing tablets prepared by physical granulation to those prepared by wet granulation. It is apparent from this data that dry granulation produces a tablet that is overall much more stable than one produced through wet granulation.

TABLE XV

RKAP TABLET STABILITY COMPARISON AS A FUNCTION OF GRANULATION

Conditions: Temperature 5° C.

| | | COMPONENT | | | | | | | | |
|---|---|---|---|---|---|---|---|---|---|---|
| TABLET | DAYS | HIS (%) | HMTB (%) | KIC (%) | KIV (%) | KMV (%) | LYS (%) | ORN (%) | THR (%) | TRP (%) | TYR (%) |
| A | 0 | 96.1 | 95.3 | 99.4 | 96.5 | 93.2 | 99.3 | 96.7 | 99.0 | 115.1 | 94.5 |
|   | 29 | 95.1 | 94.5 | 98.1 | 97.0 | 94.2 | 98.7 | 95.9 | 97.1 | 112.7 | 94.1 |
|   | 70 | 96.2 | 96.0 | 97.4 | 95.7 | 93.7 | 98.8 | 97.1 | 98.1 | 109.6 | 93.9 |
|   | 98 | 94.8 | 96.1 | 98.9 | 98.4 | 95.6 | 101.4 | 99.6 | 101.0 | 114.3 | 96.5 |
| B | 0 | 90.3 | 94.5 | 95.2 | 100.0 | 90.2 | 103.1 | 99.9 | 104.2 | 103.7 | 97.3 |
|   | 28 | 90.2 | 93.2 | 93.7 | 101.5 | 89.2 | 103.3 | 99.7 | 103.7 | 101.9 | 97.5 |
|   | 56 | 90.5 | 92.5 | 93.6 | 99.1 | 87.3 | 103.6 | 100.4 | 103.1 | 95.0 | 97.1 |

TABLE XV-continued

RKAP TABLET STABILITY COMPARISON AS A FUNCTION OF GRANULATION
Conditions: Temperature 5° C.

| TABLET | DAYS | HIS (%) | HMTB (%) | KIC (%) | KIV (%) | KMV (%) | LYS (%) | ORN (%) | THR (%) | TRP (%) | TYR (%) |
|---|---|---|---|---|---|---|---|---|---|---|---|
| | 91 | 88.1 | 93.8 | 91.5 | 95.6 | 85.9 | 103.2 | 99.1 | 101.4 | 94.6 | 96.7 |

A = Physical Granulation
B = Wet Granulation

TABLE XVI

RKAP TABLET STABILITY COMPARISON AS A FUNCTION OF GRANULATION
Conditions: Temperature 43° C.

| TABLET | DAYS | HIS (%) | HMTB (%) | KIC (%) | KIV (%) | KMV (%) | LYS (%) | ORN (%) | THR (%) | TRP (%) | TYR (%) |
|---|---|---|---|---|---|---|---|---|---|---|---|
| A | 0 | 97.5 | 96.4 | 99.4 | 98.2 | 95.2 | 101.3 | 98.7 | 97.0 | 113.9 | 97.1 |
|   | 6 | 96.3 | 97.3 | 93.1 | 98.3 | 94.8 | 101.7 | 99.9 | 99.0 | 115.3 | 99.6 |
|   | 13 | 95.8 | 97.0 | 84.3 | 98.4 | 93.3 | 100.9 | 100.0 | 102.4 | 112.0 | 100.7 |
|   | 17 | 93.2 | 96.7 | 79.2 | 100.6 | 92.6 | 99.9 | 99.1 | 99.5 | 112.3 | 99.8 |
| B | 0 | 90.3 | 94.5 | 95.2 | 100.0 | 90.2 | 103.1 | 99.9 | 104.2 | 103.7 | 97.3 |
|   | 7 | 80.9 | 89.1 | 81.0 | 98.4 | 88.2 | 104.5 | 101.6 | 108.5 | 92.2 | 100.9 |
|   | 14 | 77.4 | 85.1 | 71.5 | 92.9 | 83.4 | 104.9 | 101.6 | 111.8 | 88.9 | 103.0 |

A = Physical Granulation
B = Wet Granulation

INDUSTRIAL APPLICABILITY

Special problems are associated with the formation of tablets from mixtures of amino acids, keto acids and polypeptides. The formulations known to be beneficial to renal patients are also very sensitive to thermal degradation. Through the process disclosed herein useful tablets can be produced that provide convenience and efficacy to the patient. This invention fulfills a need that the medical community has been searching for.

While preferred embodiments have been shown and described above, persons skilled in the art will readily appreciate that various changes and modifications may be made without departing from spirit and scope of the present invention, which is defined in the following claims.

What is claimed is:

1. A method of preparing a tablet from a powdered mixture, said method comprising the following steps:
   (a) obtaining a powdered mixture comprising at least one material selected from the group consisting of amino acids, keto acids and conjugates and salts thereof; and polypeptides;
   (b) subjecting said powdered mixture to a compaction carried out over sufficient time and at sufficient pressure so as to remove air from said powder and cause physical granulation in said powder and yielding a compacted material containing granules, wherein said compaction comprises raising the pressure on said powdered mixture from about 400 p.s.i. to a pressure in the range of about 600 p.s.i., within a period of time in the range of from about 1 second to about 5 second and wherein the size of said granules is in the range of from about 149 microns to about 2,000 microns;
   (c) liberating said granules from said compacted material;
   (d) compressing said granules resulting from step (c) into a tablet; and
   (e) providing said tablet with a coating.

2. A method of preparing a tablet from a powdered mixture for the treatment of chronic renal failure, said method comprising:
   (a) obtaining a powdered mixture comprising the following components present in the following percentage by weight ranges:

| | |
|---|---|
| L-ORNITHINE α-KETOISOVALERATE | 20-25 |
| L-ORNITHINE α-KETOISOCAPROATE | 20-25 |
| L-LYSINE α-KETO-β-METHYLVALERATE | 20-25 |
| L-HISTIDINE α-KETOISOCAPROATE | 5-9 |
| CALCIUM, SODIUM OR POTASSIUM SALT OF α-HYDROXY-γ-METHYLTHIOBUTYRATE | 1-3 |
| L-TRYPTOPHAN | 0.1-1 |
| L-TYROSINE | 15-20 |
| L-THREONINE | 3-7; |

(b) subjecting said powdered mixture to a compaction over a sufficient period of time and at a sufficient pressure so as to remove air from said powder mixture and cause physical granulation in said powdered mixture and yielding a compacted material containing granules wherein said compaction comprises raising the pressure on said powdered mixture from about 400 p.s.i. to a pressure in the range of about 600 p.s.i., within a period of time in the range of from about 1 second to about 5 second and wherein the size of said granules is in the range of from about 149 microns to about 2,000 microns;
   (c) milling said material so as to liberate said granules from said compacted material;
   (d) compressing said granules resulting from step (c) into a tablet; and
   (e) providing said tablet with a coating.

3. A method of preparing a tablet from a powder mixture for the treatment of chronic renal failure, said method comprising:
   (a) obtaining a powdered mixture comprising the following components present in the following percentage by weight ranges:

| | |
|---|---|
| L-ornithine αketoisovalerate | 21-24% |
| L-ornithine α-keto-β-methylvalerate | 21-24% |
| L-lysine α-ketoisocaproate | 21-24% |
| L-histidine α-ketoisocaproate | 6-8% |
| calcium, sodium or potassium salt of α-hydroxy-γ-methylithiobutyrate | 1.5-2.5% |
| L-tryptophan | 0.2-0.75% |
| L-tyrosine | 16-19% |
| L-threonine | 4-6% |

(b) subjecting said powdered mixture to a compaction over a sufficient period of time and at a sufficient pressure so as to remove air from said powder mixture and cause physical granulation in said powdered mixture and yielding a compacted material containing granules wherein said compaction comprises raising the pressure on said powdered mixture from about 400 p.s.i. to a pressure in the range of about 600 p.s.i., within a period of time in the range of from about 1 second to about 5 second and wherein the size of said granules is in the range of from about 149 microns to about 2,000 microns;

(c) milling said material so as to liberate said granules from said compacted material;

(d) compressing said granules resulting from step (c) into a tablet; and (e) providing said tablet with a coating.

4. A method according to claim 1 wherein the granules of step (c) are removed from fines by sifting prior to being compressed into a tablet.

5. A method according to claim 1 wherein said granules are admixed with at least one excipient material prior to being compressed into a tablet.

6. A method according to claim 5 wherein said at least one excipient material comprises talc, magnesium stearate, microcrystalline cellulose, calcium phosphate, maltodextrin and soy fiber.

7. A method according to claim 1 wherein said granules are admixed with at least one disintegrant material prior to being compressed into a tablet.

8. A method according to claim 7 wherein the disintegrant material comprises sodium starch glycolate.

9. A method according to claim 1 additionally comprising the step of applying a subcoating material to said tablet prior to providing said tablet with said coating.

10. A method according to claim 2 wherein said granules are mixed with at least one excipient material prior to being compressed into a tablet, said excipient material is selected from talc, magnesium stearate, microcrystalline cellulose and mixtures thereof.

11. A method of treatment comprising administering an effective number of tablets prepared in accordance with claim 1 to a patient in need of such treatment.

12. A method according to claim 10 wherein said microcrystalline cellulose has a moisture content in the range of from about 0.75% to about 1.25% by weight.

13. A method according to claim 2 additionally comprising the step of applying a subcoating material to said tablet prior to providing said tablet with said coating.

14. A method according to claim 13 where said subcoating material comprises titanium dioxide.

15. A method according to claim 2 wherein said powdered mixture comprises the following components present at the following percentage by weight:

| | |
|---|---|
| L-ORNITHINE α-KETOISOVALERATE | 22.5 |
| L-ORNITHINE α-KETOISOCAPROATE | 22.2 |
| L-LYSINE α-KETO-β-METHYLVALERATE | 23.4 |
| L-HISTIDINE α-KETOISOCAPROATE | 6.9 |
| CALCIUM α-HYDROXY-γ-METHYLTHIOBUTYRATE | 2.1 |
| L-TRYPTOPHAN | 0.3 |
| L-TYROSINE | 17.5 |
| L-THREONINE | 5.1 |

16. A tablet prepared in accordance with the method of claim 2.

17. A method of treatment comprising administering an effective amount of a tablet prepared in accordance with claim 2 to patient in need of such treatment.

* * * * *

UNITED STATES PATENT AND TRADEMARK OFFICE
CERTIFICATE OF CORRECTION

PATENT NO. : 5,234,696
DATED : August 10, 1993
INVENTOR(S) : K. VanScoik, R. Keske, K. Cipollo, J. Weis It is certified that error appears in the above-indentified patent and that said Letters Patent is hereby corrected as shown below:

Column 1, Line 22, "table" should be -- tablet --

Column 3, Line 62, "mitures" should be --mixtures--

Column 7, Line 11, "acrinym" should be --acronym--

Signed and Sealed this

Twenty-ninth Day of March, 1994

Attest:

BRUCE LEHMAN

*Attesting Officer*     *Commissioner of Patents and Trademarks*